United States Patent
Kanz et al.

(10) Patent No.: US 8,029,447 B2
(45) Date of Patent: Oct. 4, 2011

(54) MULTIPURPOSE HOST SYSTEM FOR INVASIVE CARDIOVASCULAR DIAGNOSTIC MEASUREMENT ACQUISITION INCLUDING AN ENHANCED DYNAMICALLY CONFIGURED GRAPHICAL DISPLAY

(75) Inventors: William Russell Kanz, Woodinville, WA (US); Bruce Richard Chapman, Folsom, CA (US); Howard David Alpert, El Dorado Hills, CA (US)

(73) Assignee: Volcano Corporation, San Diego, CA (US)

( * ) Notice: Subject to any disclaimer, the term of this patent is extended or adjusted under 35 U.S.C. 154(b) by 244 days.

(21) Appl. No.: 11/870,308

(22) Filed: Oct. 10, 2007

(65) Prior Publication Data

US 2008/0269572 A1 Oct. 30, 2008

Related U.S. Application Data

(60) Provisional application No. 60/828,961, filed on Oct. 10, 2006.

(51) Int. Cl.
*A61B 5/02* (2006.01)
(52) U.S. Cl. ........ 600/483; 600/485; 600/486; 600/481; 600/504; 600/505
(58) Field of Classification Search .................. 600/481, 600/483–485, 486, 488, 504–507
See application file for complete search history.

(56) References Cited

U.S. PATENT DOCUMENTS

| | | | |
|---|---|---|---|
| 6,188,407 B1 * | 2/2001 | Smith et al. | 715/841 |
| 6,220,098 B1 * | 4/2001 | Johnson et al. | 73/592 |
| 6,322,502 B1 * | 11/2001 | Schoenberg et al. | 600/300 |
| 7,134,994 B2 * | 11/2006 | Alpert et al. | 600/300 |
| 7,612,679 B1 * | 11/2009 | Fackler et al. | 340/573.1 |
| 7,643,862 B2 * | 1/2010 | Schoenefeld | 600/407 |
| 2003/0216621 A1 * | 11/2003 | Alpert et al. | 600/300 |
| 2004/0059203 A1 * | 3/2004 | Guerrero et al. | 600/300 |
| 2004/0169673 A1 * | 9/2004 | Crampe et al. | 345/700 |
| 2007/0060822 A1 * | 3/2007 | Alpert et al. | 600/481 |

\* cited by examiner

*Primary Examiner* — Miranda Le
*Assistant Examiner* — Navin Natnithithadha
(74) *Attorney, Agent, or Firm* — Haynes and Boone, LLP

(57) ABSTRACT

The present invention provides a multipurpose host system for processing and displaying invasive cardiovascular diagnostic measurement data. The system includes a an external input signal bus interface. The bus interface receives data arising from cardiovascular diagnostic measurement sensors. Measurement processing components receive data from particular sensor types. Based on the received data, the processing components render diagnostic measurement parameter values. A multi-mode graphical user interface includes display components corresponding to data received from particular sensor types. The user interface provides recommended action prompts that guide a user through a series of actions.

21 Claims, 16 Drawing Sheets

MULTIPURPOSE HOST SYSTEM FOR INVASIVE CARDIOVASCULAR DIAGNOSTIC MEASUREMENT ACQUISITION INCLUDING AN ENHANCED DYNAMICALLY CONFIGURED GRAPHICAL DISPLAY

CROSS-REFERENCE TO RELATED APPLICATION

This application claims priority to Kanz (et al) U.S. Provisional Application Ser. No. 60/828,961, entitled "MULTIPURPOSE HOST SYSTEM FOR INVASIVE CARDIOVASCULAR DIAGNOSTIC MEASUREMENT ACQUISITION INCLUDING AN ENHANCED DYNAMICALLY CONFIGURED GRAPHICAL DISPLAY", the contents of which are expressly incorporated by reference in their entirety, including any references contained therein.

AREA OF THE INVENTION

The present invention generally relates to the area of diagnostic medical equipment, and more particularly to diagnostic devices for identifying and/or verifying efficacy of treatment of problematic blockages within coronary arteries by means of sensors mounted upon the end of a flexible elongate member such as a guide wire or a catheter.

BACKGROUND OF THE INVENTION

Innovations in diagnosing and verifying the level of success of treatment of cardiovascular disease have migrated from external imaging processes to internal, catheterization-based, diagnostic processes. Diagnosis of cardiovascular disease has been performed through angiogram imaging wherein a radiopaque dye is injected into a vasculature and a live x-ray image is taken of the portions of the cardiovascular system of interest. Magnetic resonance imaging (MRI) has also been utilized to non-invasively detect cardiovascular disease. Diagnostic equipment and processes also have been developed for diagnosing vasculature blockages and other vasculature disease by means of ultra-miniature sensors placed upon a distal end of a flexible elongate member such as a catheter, or a guide wire used for catheterization procedures.

One such ultra-miniature sensor device is a pressure sensor mounted upon the distal end of a guide wire. An example of such a pressure sensor is provided in Corl et al. U.S. Pat. No. 6,106,476, the teachings of which are expressly incorporated herein by reference in their entirety. Such intravascular pressure sensor measures blood pressure at various points within the vasculature to facilitate locating and determining the severity of stenoses or other disrupters of blood flow within the vessels of the human body. Such devices are presently used to determine the need to perform an angioplasty procedure by measuring blood pressure within a vessel at multiple locations, including both upstream and downstream of a stenosis and measuring a pressure difference that indicates the severity of a partial blockage of the vessel.

In particular, a guide wire mounted pressure sensor is utilized to calculate fractional flow reserve (or "FFR"). In the coronary arteries, FFR is the maximum myocardial flow in the presence of stenosis divided by the normal maximum myocardial flow. This ratio is approximately equal to the mean hyperemic (i.e., dilated vessel) distal coronary pressure Pd divided by the mean arterial pressure Pa. Pd is measured with a pressure sensor mounted upon a distal portion of guide wire or other flexible elongate member after administering a hyperemic agent into the blood vessel causing it to dilate. Pa is measured using a variety of techniques in areas proximal of the stenosis, for example, in the aorta.

FFR provides a convenient, cost-effective way to assess the severity of coronary and peripheral lesions, especially intermediate lesions. FFR provides an index of stenosis severity that allows rapid determination of whether an arterial blockage is significant enough to limit blood flow within the artery, thereby requiring treatment. The normal value of FFR is about 1.0. Values less than about 0.75 are deemed significant and require treatment. Treatment options include angioplasty and stenting.

Another such known ultra-miniature sensor device is a Doppler blood flow velocity sensor mounted upon the end of a guide wire. Such device emits ultrasonic waves along the axis of a blood vessel and observes a Doppler-shift in reflected echo waves to determine an approximation of instantaneous blood flow velocity. A Doppler transducer is shown in Corl et al. U.S. Pat. No. 6,106,476 on a guide wire that also carries a pressure transducer. Such devices are presently used to determine the success of a treatment to lessen the severity of a vessel blockage.

In particular, a Doppler transducer sensor is utilized to measure Coronary Flow Reserve (or "CFR"). CFR is a measure for determining whether a stenosis is functionally significant after treatment (e.g., post-angioplasty). CFR comprises a ratio of the hyperemic average peak velocity of blood flow to the baseline (resting) average peak velocity. Instantaneous peak velocity (IPV) is the peak observed velocity for an instantaneous Doppler spectrum provided by a Doppler transducer. An exemplary method of calculating an average peak velocity (APV) comprises averaging a set of IPV's over a cardiac cycle.

A known technique for determining whether an angioplasty was effective was to perform angioplasty, wait a few days, then perform thallium scintigraphy (imaging). If the angioplasty procedure was not effective, then re-intervention was performed and the lesion was again treated via angioplasty. On the other hand, using CFR, a flow measurement is taken immediately after angioplasty or stenting. The flow measurement is utilized to determine whether adequate flow has been restored to the vessel. If not, the balloon is inflated without the need for secondary re-intervention. A normal CFR is greater than about 2 and indicates that a lesion is not significant. Lower values may require additional intervention. In addition to being used post-treatment to determine the efficacy of treatment, CFR may be measured prior to treatment to determine if treatment is required.

A guide wire combination device, comprising a pressure sensor and a flow sensor having substantially different operational characteristics, was disclosed in the Corl et al. U.S. Pat. No. 6,106,476. While it has been proposed within the Corl et al. U.S. Pat. No. 6,106,476 to combine pressure and flow sensors on a single flexible elongate member, the prior art does not address how such a combination sensor is coupled to consoles that display an output corresponding to the signals provided by the flexible elongate member corresponding to the sensed pressure and flow within a vessel. Indeed, in known systems special-purpose monitors having static display interfaces that display a static set of parameters corresponding to a particular fixed set of diagnostic measurements (e.g., an aortic pressure and a pressure taken from a location proximate a stenosis). Thus, one type of monitor is utilized to process and display sensed pressure within a blood vessel. Another type of monitor provides output relating to blood flow within a vessel. As new intravascular diagnostic devices are developed, yet other special-purpose monitors/consoles are developed to display to a physician the sensed parameters.

There is substantial interest in simplifying every aspect of the operating room to reduce the incidence of errors. As one can imagine, the aforementioned intravascular pressure sensors are utilized in operating room environments including many types of sensors and equipment for diagnosing and treating cardiovascular disease. Clearly, the room for error is very limited when performing such activities. Notwithstanding the interest to keep equipment and operations simple, there exists a variety of different sensors that are potentially inserted within a human vasculature to diagnose arterial disease (e.g., blockages) and/or monitor vital signs during a medical procedure. The approach taken in the field of interventional cardiac imaging has been to provide multiple, special-purpose monitor consoles. Each monitor type is linked to a particular type of sensor device.

In a known prior intravascular pressure sensor-to-physiological monitor interface arrangement, marketed by JOMED Inc. of Rancho Cordova, Calif., a physiology monitor receives and displays, on a permanently configured display interface, a set of pressure values corresponding to two distinct pressure signals that are received by the monitor. A first pressure signal is provided by an aortic pressure sensor, and a second pressure signal corresponds to a pressure sensed by a distally mounted solid-state pressure sensor mounted upon a guide wire. The display interface of the monitor is permanently configured to output parameter values corresponding to those two signals. Thus, if display of, for example, a flow signal value is desired, then a separate monitor, such as JOMED Inc.'s FloMap, is used. More recently, a multipurpose user interface application/system is provided. An example of such a system is described in Alpert et al. U.S. Pat. No. 7,134,994

SUMMARY OF THE INVENTION

The present invention provides a multipurpose host system for processing and displaying invasive cardiovascular diagnostic measurement data. The system includes an external input signal bus interface. The bus interface receives data arising from cardiovascular diagnostic measurement sensors. Measurement processing components receive data from particular sensor types. Based on the received data, the processing components render diagnostic measurement parameter values. A multi-mode graphical user interface includes display components corresponding to data received from particular sensor types. The user interface provides recommended action prompts that guide a user through a series of actions. The measurement sensors, by way of example, include a blood pressure processing sensor and a blood velocity sensor. The user interface provides recommended action prompts, by way of example, by altering the appearance of graphical elements on the display.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

DETAILED DESCRIPTION OF THE DRAWINGS

A multipurpose host system for invasive cardiovascular diagnostic measurement acquisition and display presents multiple user display interfaces. Each of the display interfaces corresponds to a particular purpose for which the multipurpose host is currently configured based, for example, upon one or more sensor devices communicatively coupled to its external signal interface. The host system is used, for example, in conjunction with interventional cardiology, e.g., angiography, or interventional procedures, e.g., angioplasty, to evaluate the hemodynamic status of an arterial blockage. The present system includes an enhanced user interface that guides users through various tasks. In some embodiments the system automatically displays appropriate user interfaces based on the sensor connected to the host system.

Figure 1:
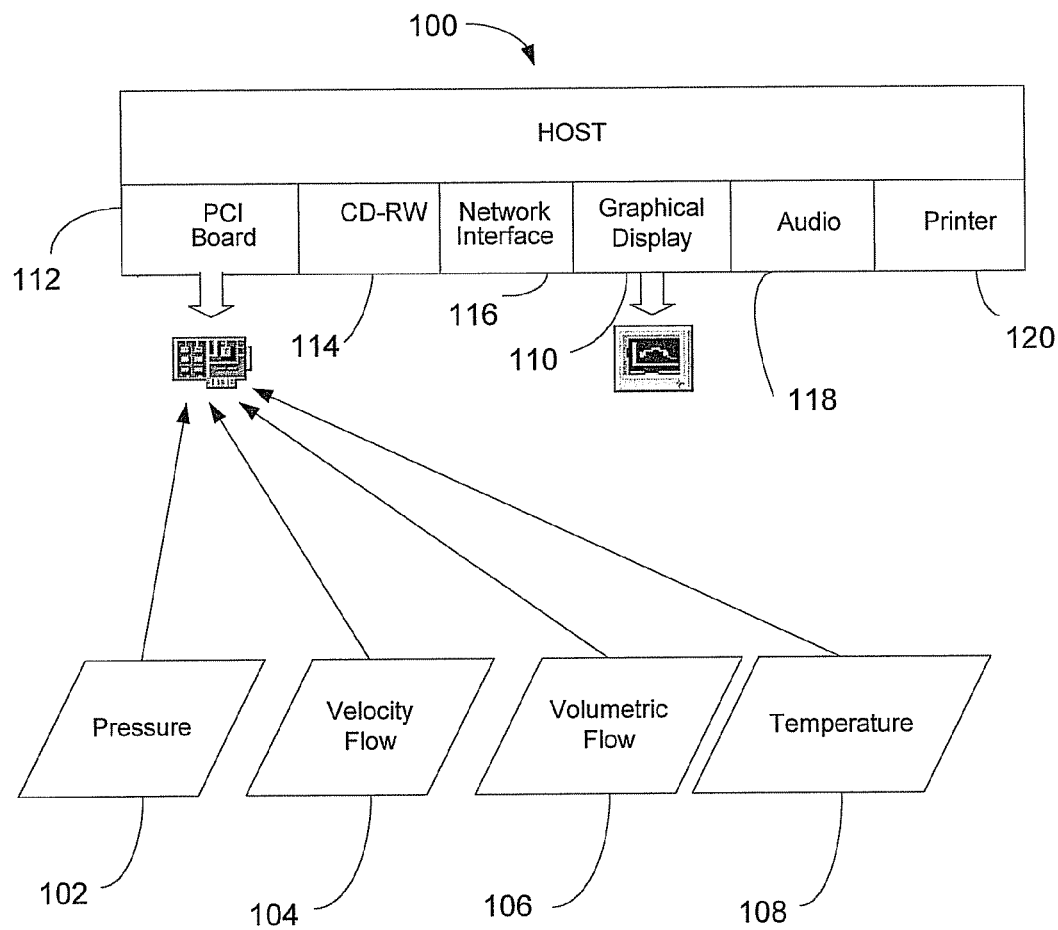
FIG. 1 is a schematic drawing depicting a system for conducting invasive cardiovascular diagnoses including an external input signal interface for receiving diagnostic parameter values of multiple types and a multimode graphical user interface for presenting the values according to a user-selected one of the multiple display modes.

With reference to FIG. 1, a multipurpose host system 100 is, by way of example, a personal computer architecture-based system for assessing real-time invasive cardiovascular parameters from within a blood vessel (e.g., blood pressure and flow measurements). An example of such a host system is provided in Alpert et al. U.S. Pat. No. 7,134,994, the teachings of which are expressly incorporated herein by reference in their entirety. The multipurpose host processes input signals from multiple micro-miniature guide wire-mounted sensors (e.g., Doppler and pressure transducers) to produce real-time measurements, display various waveforms and derived parameters, and output high-level voltages proportional to calculated parameter values. The devices that supply the various data input signals are represented by pressure input 102, velocity flow input 104, volume flow 106, and temperature input 108. In an embodiment of the invention, the devices that provide the input to the host system 110 are presently used in existing, special-purpose processing boxes. This set is exemplary, as those skilled in the art will readily appreciate in view of this disclosure that alternative systems advantageously receive and process such diagnostic inputs as pH, ultrasound and light-based cross-sectional images of a vessel, biochemical markers, light spectrometry for tissue characterization, etc. It is further noted that the displayed output of the host system 100 is not limited to producing the measured parameters. Rather, the various modes of the host system 100 are capable of synthesizing generalized measures of physiological status (e.g., whether a blockage is severe and needs treatment) based upon the input parameter values.

The host system 100 operates in a plurality of modes, and each mode includes its own distinct graphical interface (rendered on graphical output display 110) and input parameter values (provided via a peripheral component interconnect (PCI) card 112) corresponding to particular sensor types. The PCI card 112 includes, by way of example, a digital signal processor (DSP) that samples data provided by the communicatively coupled input sensors and processes the sampled data to render digital data in a format expected by higher level components of the host system 100. Exemplary processes performed by the DSP include: A/D and D/A conversions, FFTs, level shifting, normalizing, and scaling. After processing the data, it is stored in a dual port RAM accessed, via the PCI bus of the host 100, by higher level application processes executing on the host system 100.

In the exemplary embodiment, input sensor types driving the output displays include pressure, flow, and temperature sensors mounted upon a flexible elongate member including combinations thereof placed, for example, upon a single guide wire or catheter. In fact, the flexible module-based architecture of the exemplary host system 110, which supports simultaneous display of multiple distinct types of input signals on a single graphical user interface, is particularly well suited for such combination devices since their output can be simultaneously monitored on a single interface even though modules that process the sensor inputs execute independently within the host system 100.

The exemplary host system 100 operates in pressure, flow, and combination (pressure/flow) modes. Though not essential to the invention, operation of each mode is preferably independent of the other modes, and each diagnostic display mode is driven by a designated set of parameter generation modules associated with particular input signals received by the host system from a communicatively coupled sensor. The pressure mode provides the user with a selection of calculated/derived parameters such as for example: proximal-distal pressure gradient, distal/proximal pressure ratio, normalized pressure ratio, and fractional flow reserve (normalized pressure ratio under hyperemic conditions). In an exemplary embodiment, the flow mode is divided into three operational modes: peripheral, coronary, and research. The peripheral mode acquires measurements in the cerebral or peripheral vasculature. The coronary mode acquires measurements in the coronary arteries. The research mode provides a superset of peripheral and coronary modes plus additional parameters that may be of interest in a clinical research environment. The combination mode allows parameters associated with pressure and flow modes to be displayed simultaneously on a single graphical display.

In the illustrative embodiment of the invention, the graphical display interface 110 depicts calculated pressure and flow information on a strip chart graph on a graphical user interface display. The current values are, for example, displayed numerically as well. The graph scrolls as new information is calculated and added. A graphically displayed control enables a user to freeze the scrolling graphs and scroll backwards to view previously displayed portions of the scrolling graph. Additional display methods and techniques will be apparent to those skilled in the art.

In the illustrative example, the host system 100 embodies an extensible, component-based architecture, and thus the host system 100 supports a virtually limitless number of operating modes for processing and rendering graphical display output corresponding to an extensible set of input signals provided by sensors measuring a variety of types and combinations thereof. The host system 100 is modularized to support receiving and processing signals in a variety of formats from a variety of instruments. In a particular exemplary embodiment of the invention, the host system 100 relies on transducers and external diagnostic instrumentation to: (1) process the raw sensor information rendered by transducers/sensors inserted within a patient and (2) provide the information to the host 100 in particular digital or analog formats. The host system 100's capabilities are extendable, by way of example through enhancements to a currently installed peripheral component interconnect (PCI) board 110 or the addition of new PCI boards, to include additional signal processing capabilities. In an exemplary embodiment, transducers on the guide wire (patient isolated) provide low-level signals for blood velocity, flow, and pressure. A standard external pressure transducer (patient isolated) may be integrated with the host system to provide low-level aortic pressure. A high-level ECG signal input to the host provides synchronization for calculations (not patient isolated).

The interface of the host system 100 comprises a number of additional interfaces supporting the transfer and storage of information relating to the operation of the host system. Data storage device 114, for example, a CD-RW or a DVD-RW drive, is utilized to upload new software and store patient data processed and displayed during a diagnostic/treatment procedure. A network interface 116 provides remote access for performing functions similar to those provided by the data storage device 114. An audio input 118 enables annotation of input records by a user. A printer 120 facilitates printing out labels and/or compiled data from a diagnostic/treatment procedure. The set of peripheral/interface components identified in FIG. 1 is exemplary. As those skilled in the art will readily appreciate there exist a vast variety of I/O devices that can be advantageously incorporated into the host system 100 to enhance its utility. Furthermore, the above-described multipurpose host system architecture is intended to be exemplary and does not limit the broad range of system environments wherein the user interface application described herein below is potentially incorporated.

Having described the peripheral components and external interfaces of an exemplary host system 100, attention is now directed to a user interface incorporated into the exemplary multipurpose host for carrying out a variety of diagnostic/treatment procedures. The illustrative sets of user interfaces support a variety of interactive sequences of actions associated with the variety of sensors/devices connectable to the host system 100. The user interface sets are configured to facilitate a system-directed sequence of actions to acquire patient data for particular diagnostic procedures.

Figure 2:
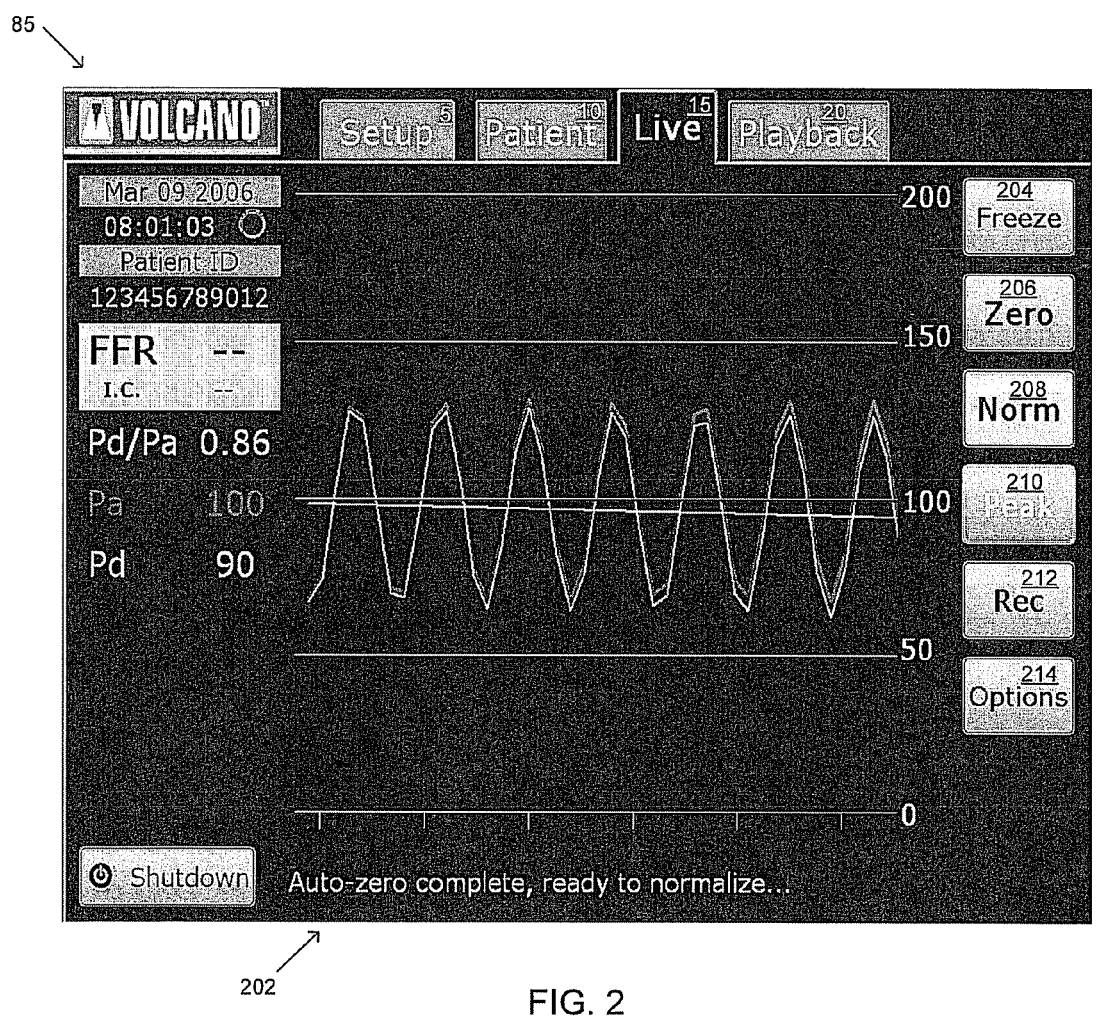
FIG. 2 depicts an exemplary graphical user interface for a system upon which signals rendered by invasive cardiovascular sensors are displayed.

FIG. 2 depicts an exemplary graphical user interface 85 of graphical display 110. The interface 85 provides a user with information tabs to input Setup information 5 and Patient information 10. Additionally, the user can view Live 15 and recorded 20 sensor information. In alternative embodiments of the invention, Setup 5 information is shown as a Settings information tab. The Setup 5 or Settings tab contains six sub-tabs that provide setup or settings information for the system, pressure sensor, flow sensor, service, research and factory information. Settings in the sub-tabs are persistent from session to session and patient to patient. Further, information in the Service, Research, and Factory sub-tabs are password protected.

Figure 3:
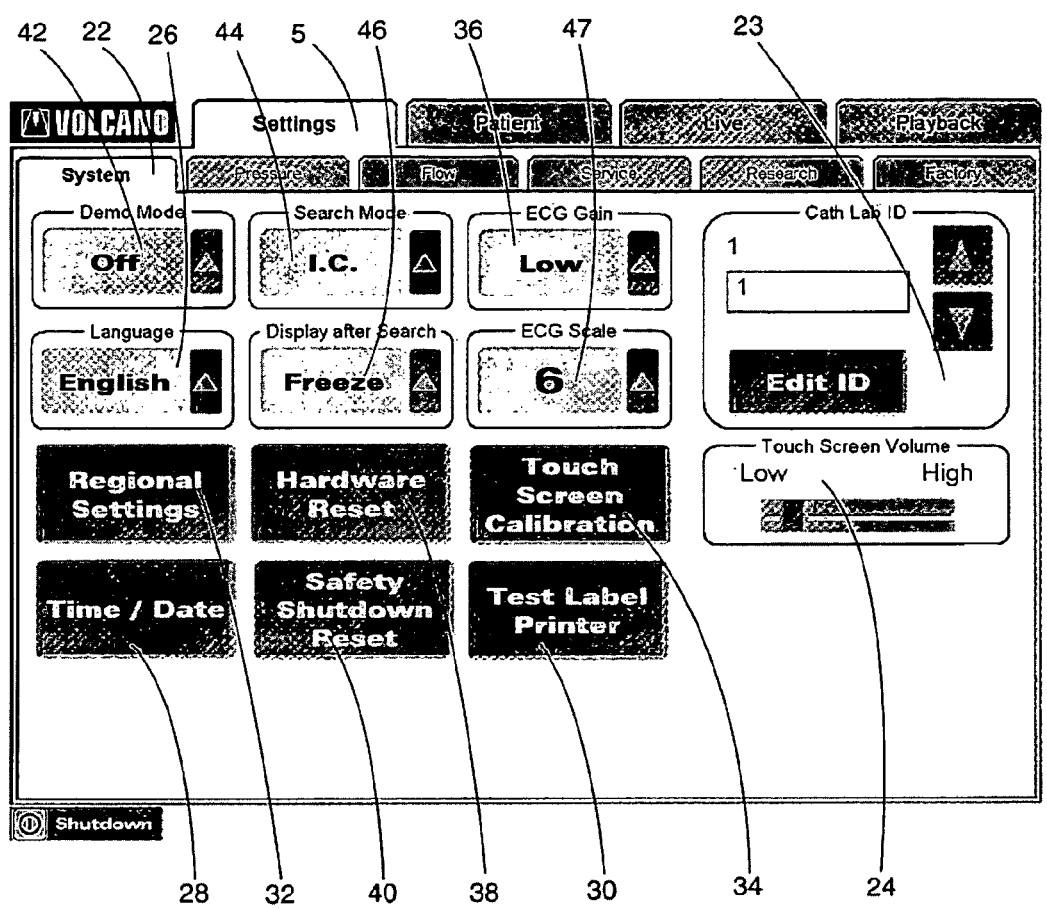
FIG. 3 depicts an exemplary graphical user interface for configuring system settings for the system.

FIG. 3 illustrates an exemplary Systems sub-tab 22 of the Settings tab 5. The Systems sub-tab includes, but is not limited to, an identification string 23, touch screen volume 24, and language selection 26, time/date 28, test label printer 30, regional settings 32, touch screen calibration 34, ECG Gain 36, Hardware Reset 38, Safety Shutdown Reset 40, Demo Mode 42, Search Mode selection 44, Display after Search selection 46 and ECG Scale selection 48. The system allows a user to select the information shown on the display interfaces in several different languages 26. Test Label Printer 30 allows a user to print a pre-configured label for diagnostics. Regional settings 32 allow a user to select a format style for the data present on the display interfaces. ECG Gain 36 allows a user to select a gain corresponding to the signal level. Hardware Reset 38 resets the DSP of the system. Safety Shutdown Reset 40 resets the hardware after the safety shutdown feature has been triggered. Demo Mode 42 allows a user to select a system demonstration mode. The Display after Search selection 46 allows the user to automatically freeze after a peak timeout or continue running after a peak timeout.

Figure 4:
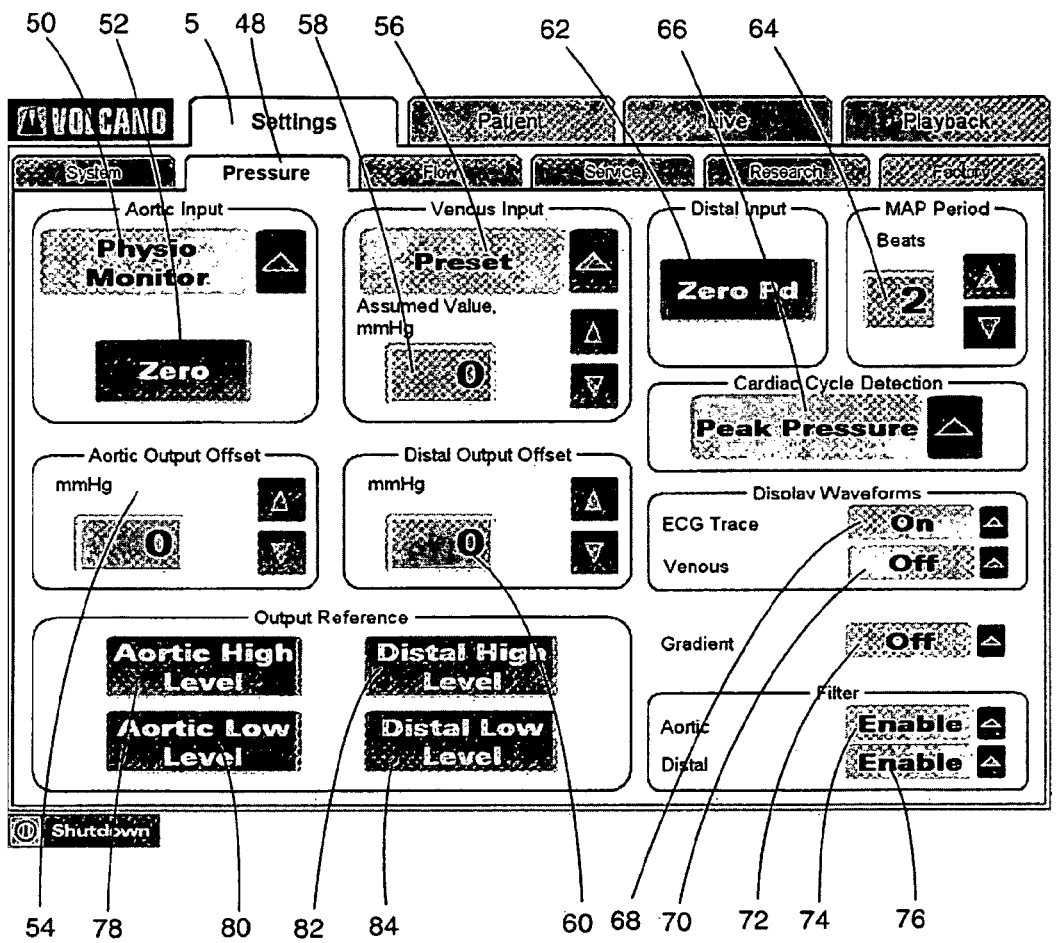
FIG. 4 depicts an exemplary graphical user interface for configuring pressure settings for the system.

FIG. 4 illustrates an exemplary Pressure sub-tab 48 of the Settings tab 5. The exemplary Pressure sub-tab 48 includes, Aortic input 50, Aortic Input Zero selection 52, Aortic Output Offset 54, Venous Input Preset 56, Venous Input Assumed Value 58, Distal Output Offset 60, Distal Input 62, MAP Period Beats 64, Cardiac Cycle Detection 66, ECG Trace Display Waveform selection 68, Venous Display Waveform selection 70, Gradient 72, Aortic Filter 74, Distal Filter 76, Output References Aortic High Level 78, Aortic Low Level 80, Distal High Level 82, and Distal Low Level 84. The ECG Trace Display Waveform selection 68 controls the display of the Heart Rate value on the Live and Playback Tab screens (see, e.g., FIGS. 2, 14, and 15). If the ECG waveform is selected for display 68, the Heart Rate value on the Live Tab Display Screen (FIG. 2) is displayed, otherwise, the Heart Rate value is not shown on the Live Tab Display or the Playback screens.

The selection of the Venous Display Waveform selection 70 controls the display of the Pv value on the Live Tab Display Screen (FIG. 2) when configured for pressure or combo modes. If the Venous waveform 70 is selected for display on the Live Tab Display Screen (FIG. 2), the Pv value is displayed on the Live Tab Display Screen. Otherwise, the Pv value is not shown on the Live Tab Display or the Playback screens.

Figure 5:
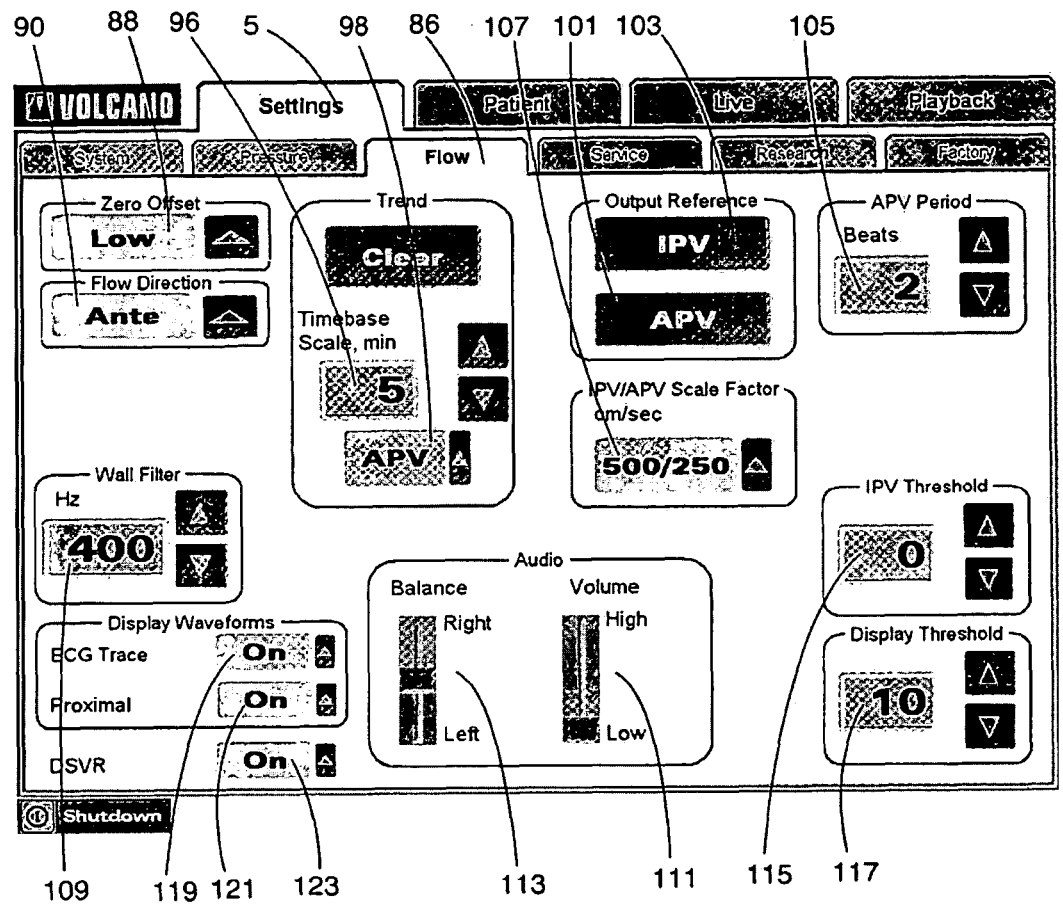
FIG. 5 depicts an exemplary graphical user interface for configuring flow settings for the system.

FIG. 5 illustrates an exemplary Flow sub-tab 86 of the Settings tab 5. The exemplary Flow sub-tab 86 includes, but is not limited to, Zero Offset selection 88, Flow Direction selection 90, Trend selection including clear 94, Timebase scale 96, and Trend select 98, Output Reference APV 101, Output Reference IPV 103, APV Period select 105, IPV/APV Scale Factor selection 107, Wall Filter selection 109, Audio Volume adjustment 111, Audio Balance adjustment 113, IPV Threshold selection 115, Display Threshold selection 117, ECG Display waveform 119, Proximal Display waveform 121 and DSVR selection 123. If the DSVR 123 is selected "On", the value shall appear on the Live and Playback displays, further described hereinafter.

Figure 6:
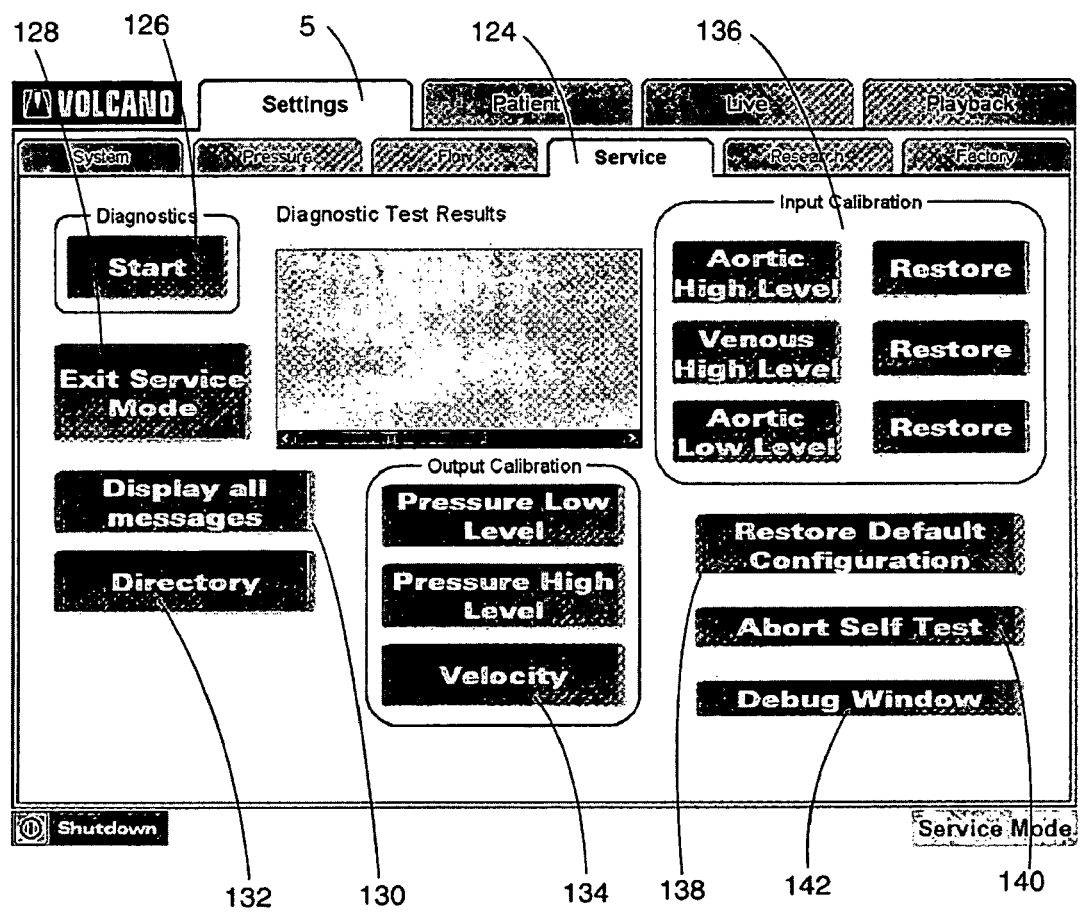
FIG. 6 depicts an exemplary graphical user interface for configuring service settings for the system.

FIG. 6 illustrates an exemplary Service Setup sub-tab 124 of the Settings tab 5. The exemplary Service sub-tab 124 includes, but is not limited to, Diagnostics Start 126, Exit Service Mode 128, Display all Messages 130, Directory 132, Output Calibration settings 134, Input Calibration settings 136, Restore Default Configuration 138, Abort Self Test 140, and Debug Window 142. The Service Setup sub-tab 124 allows users to monitor, test and diagnose issues with the system.

Figure 7:
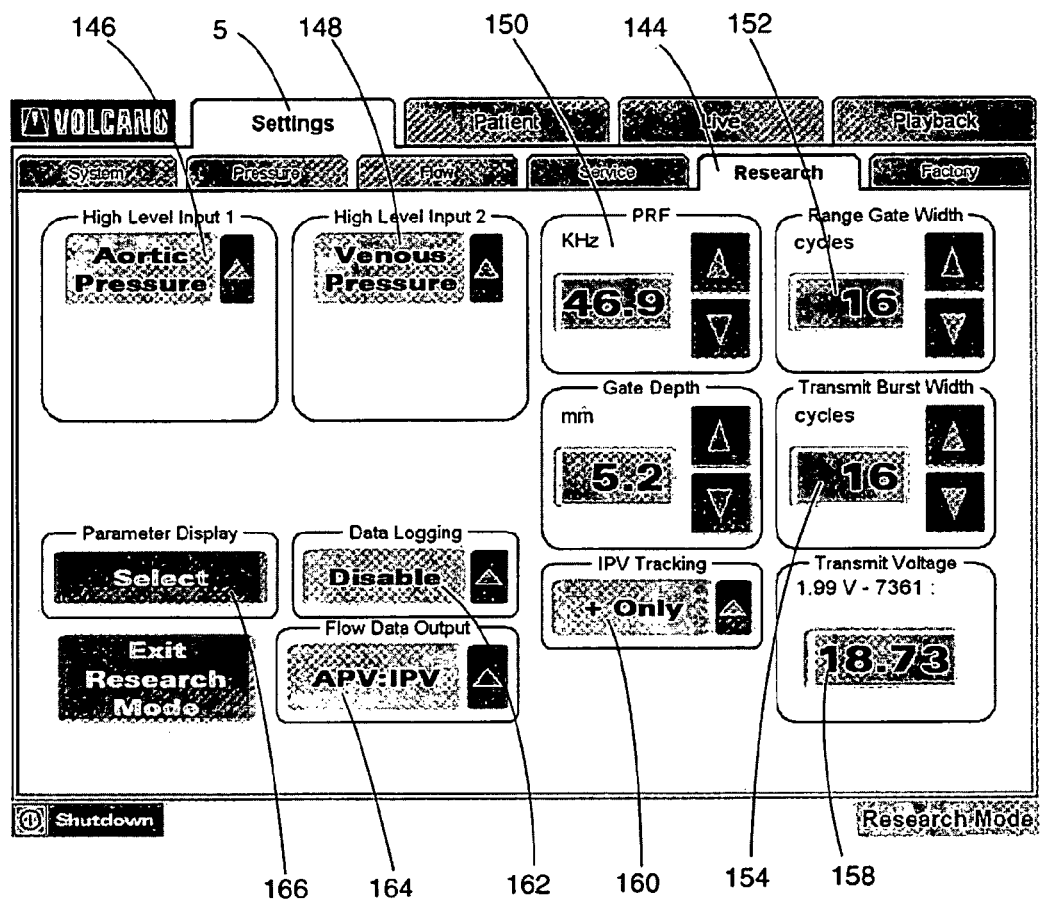
FIG. 7 depicts an exemplary graphical user interface for configuring research settings for the system.
Figure 8:
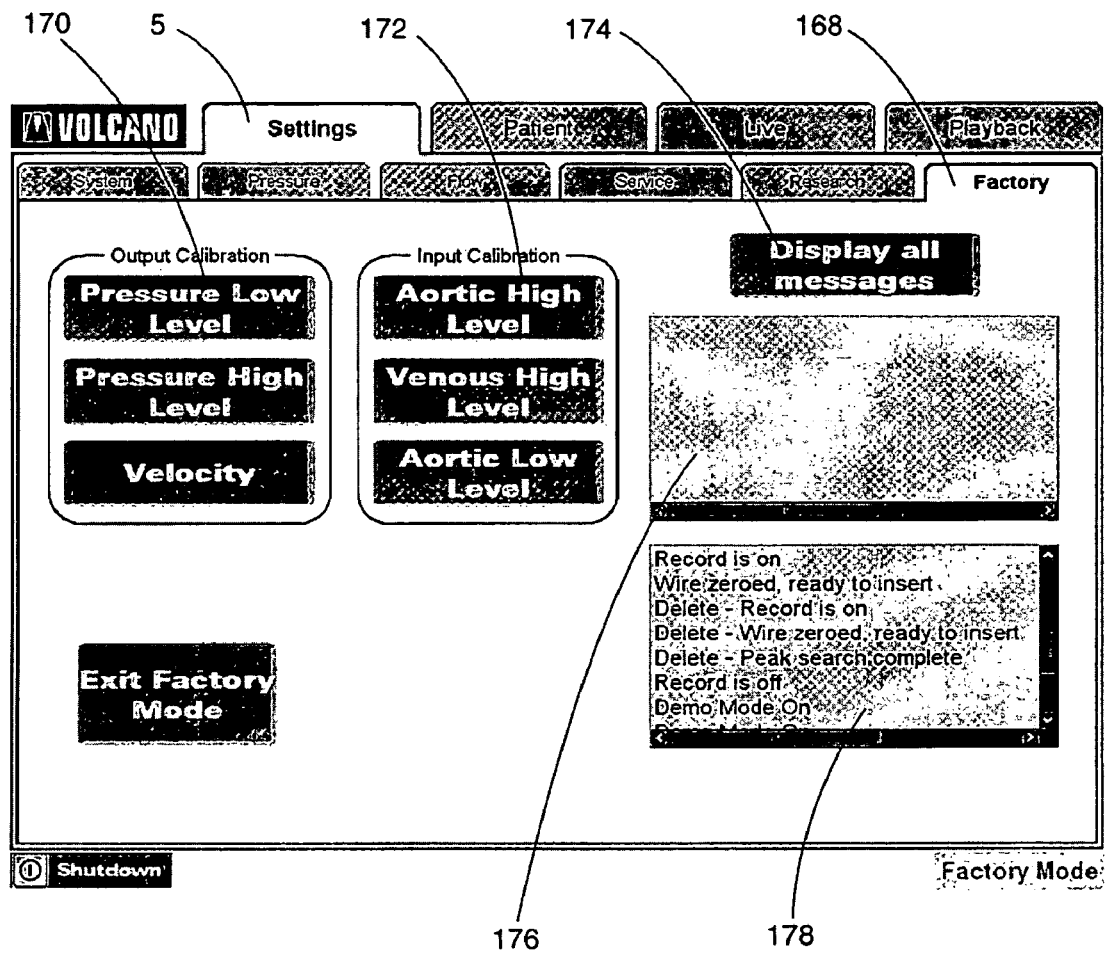
FIG. 8 depicts an exemplary graphical user interface for configuring factory settings for the system.

FIG. 7 illustrates an exemplary Research sub-tab 144 of the Settings tab 5. The exemplary Research sub-tab 144 includes, but is not limited to, High level input 1 146, High level input 2 148, PRF 150, Range Gates Width 152, Transmit Burst Width 154, Gate Depth 156, Transmit Voltage 158, IPV Tracking 160, Data Logging 162, Flow Data Output 164 and Parameter Display 166. The exemplary Research sub-tab 144 allows users to set parameters of the system. Similarly, the Factory sub-tab 168 (FIG. 8) allows users to alter parameters of the system typically configured by the system manufacturer. Exemplary Settings include, Output Calibration 170, Input Calibration 172, Display all messages 174, and Display panels 176 and 178.

Figure 9:
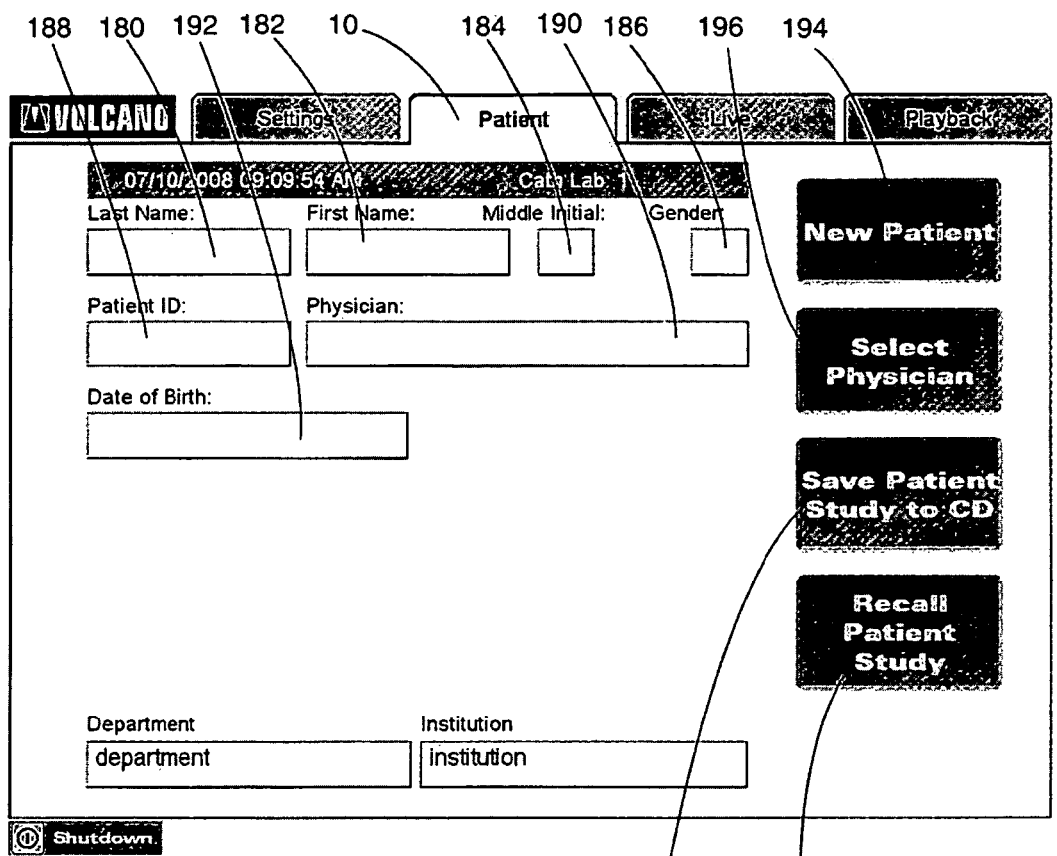
FIG. 9 depicts an exemplary graphical user interface for entering patient data into the system.

FIG. 9 illustrates an exemplary Patient tab 10. The exemplary Patient tab 10 includes fields for Last Name 180, First Name 182, Middle Initial 184, Gender 186, Patient ID 188, Physician 190 and Date of Birth 192. Inputs are also provided to create a New Patient 194, Select a Physician 196, Save a Patient Study 198 and Recall a Patient Study 200. The Patient tab allows users to manage individual patient files and track patient data.

After a user inputs the optional Setup or Settings information (FIG. 3-FIG. 8) and Patient information (FIG. 9), Live patient monitoring data may be viewed on the graphical user interface. Referring to FIG. 2, after entering the option Setup data on sub-tab and Patient data on sub-tab 10, the user may begin viewing data on the Live sub-tab 15. FIG. 2 represents an exemplary Live display for pressure data. In this example, a Zero setup has already been performed. The interface displays a message 202 notifying the user that the Zero setup has been completed. Inputs on the Live sub-tab 15 (FIG. 10) displaying pressure data include Freeze 204, Zero 206, Norm 208, Peak 210, Rec 212 and Options 214. Freeze 204 allows the user to freeze the chart interface. When the chart interface is not frozen, live data scrolls across the interface. Zero 206 calibrates the zero point aortic or proximal pressure wire. Norm 208 normalizes the distal pressure wire to the aortic pressure. Rec 212 turns on the data recording function. Options 214 allows the user to enter system parameters.

The Live sub-tab 15 enters Pressure mode when only a pressure wire is connected to the system. The screen displays data variables on the left, graph in the middle, and user buttons on the right.

In accordance with an illustrative example, the Live sub-tab 15 includes a wizard driven system to guide a user through configuring and analyzing patient data. The system indicates the next recommended action the user should perform. The system can indicate the next recommended action in any method. For example, the next action can appear as a different color on the screen or can appear in bold text. In the illustrated embodiment, the next recommended action appears highlighted in green, and no other control on the screen will have the green color at the same time. However, any appropriate method of indicating the next recommended action (or multiple actions in the event that more than one sequence of actions is available from a currently displayed user interface) can be used. For example, in FIG. 2, the next recommend action is Norm 208. Therefore Norm 208 appears green on the screen. After viewing the screen, the user knows that the wizard driven system recommends performing the Norm 208 action.

Furthermore, other appearance/user interface characteristics are used to prevent a user from initiating actions. For example, the Peak 210 step should not be performed until the Norm 208 step is completed. Therefore, Peak 210 appears faded on the screen, indicating to the user that it is not appropriate to perform the Peak 210 step.

Figure 10:
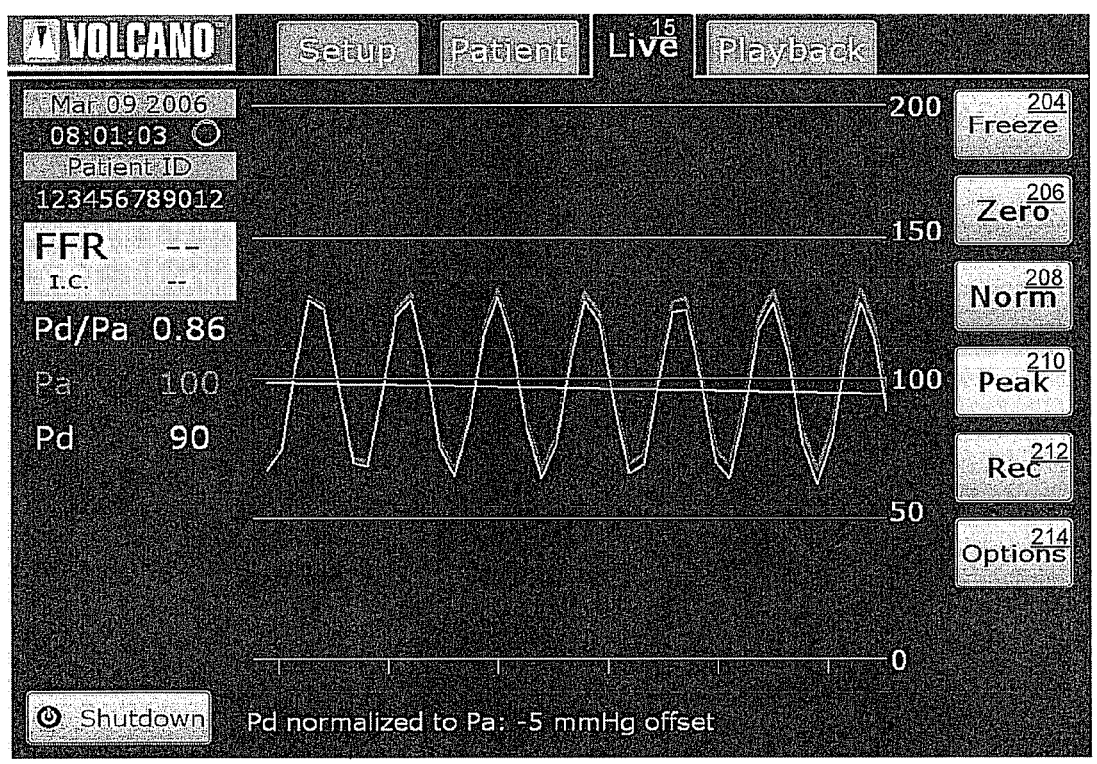
FIG. 10 depicts an exemplary graphical user interface for obtaining live data rendered by invasive cardiovascular sensors.
Figure 11:
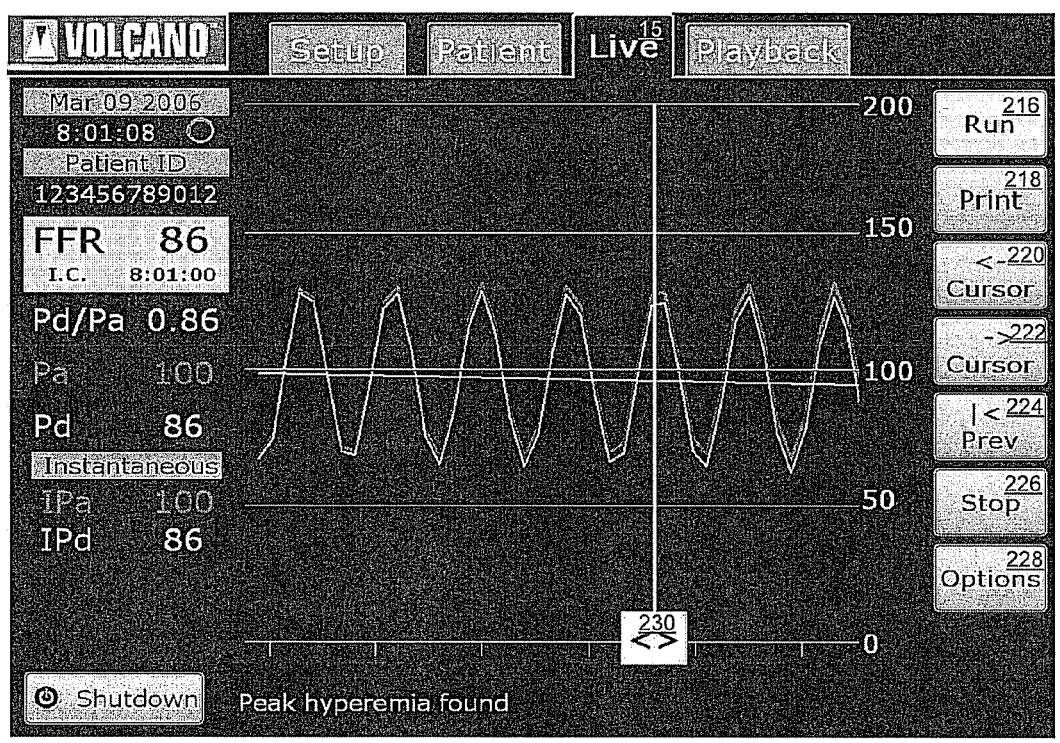
FIG. 11 illustrates an exemplary graphical user interface for determining the peak hyperemia.

After performing the Norm 208 step indicated in FIG. 2, the system recommends performing the Peak 210 step. FIG. 10 indicates that the Peak 210 step should be performed by highlighting Peak 210 in green. The user interface illustrated in FIG. 10 displays Live pressure data. After the user enters the Peak 210 mode, the peak hyperemia can be found. FIG. 11 illustrates an exemplary graphical user interface for determining the peak hyperemia. While determining the peak hyperemia, the interface is controlled by the Display after Search 46 control (FIG. 3).

The exemplary Peak interface (FIG. 11) includes Run 216 which starts and stops the chart scrolling. Print 218 prints the screen. The left cursor 220 moves the data cursor 230 left. The right cursor 222 moves the data cursor 230 right. Rec/Stop 226 starts and stops data recording. Options 228 displays a pressure options dialog. Using the data cursor 230, the peak hyperemia is shown by the system. In this example Run 216 is highlighted green, indicating that the system recommends starting the chart scrolling.

The exemplary Peak interface can display a number of different variables. For example, IC/IV—hyperemic injection type, peak time—time of day of last peak detected, Pd/Pa or NPR—distal/aortic pressure ratio with or without venous pressure normalization, Pa-Pd—gradient from aortic to distal pressure, Pa—aortic pressure mean, Pd—distal pressure mean, Pv—venous pressure mean (only if external or non-zero preset), HR—heart rate (only if ECG displayed) can all be displayed as appropriate. Additionally, when the system enters freeze 204 mode iPa—instantaneous aortic pressure (under cursor) and iPd—instantaneous distal pressure (under cursor) can be displayed.

Figure 12:
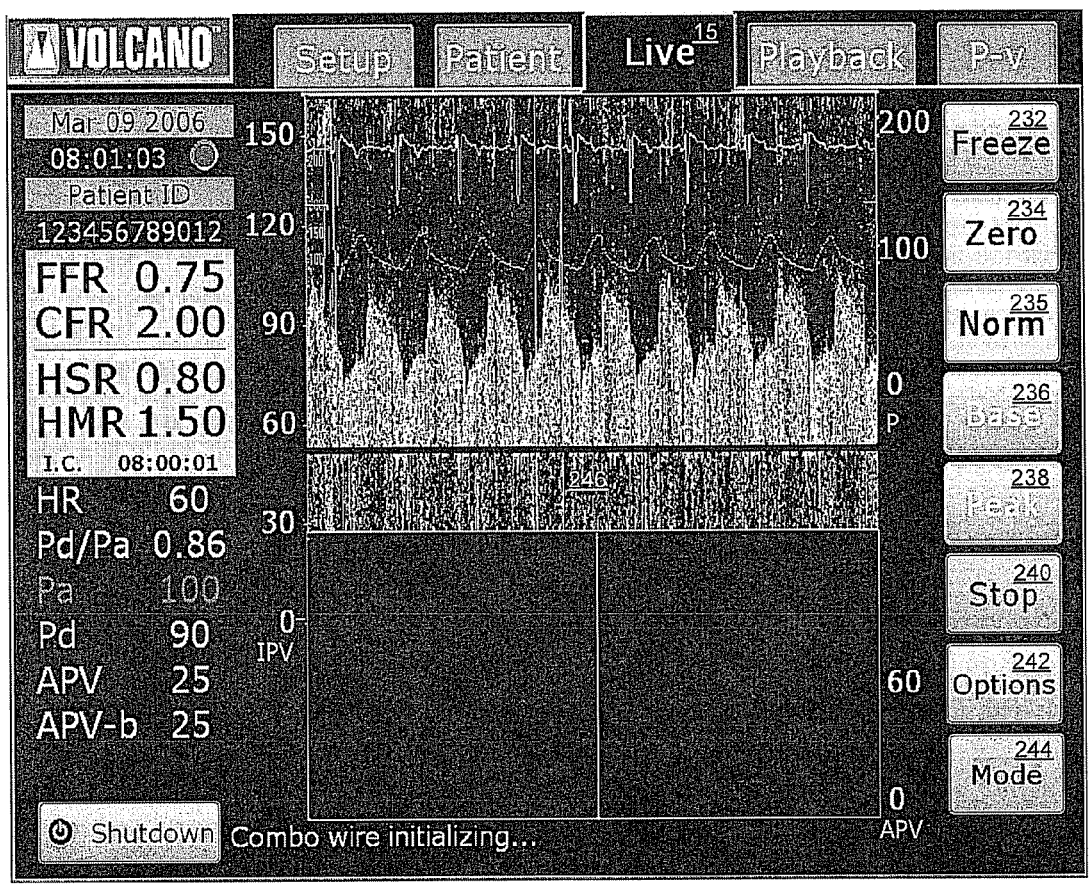
FIG. 12 illustrates an exemplary graphical user interface displaying flow and pressure data rendered by invasive cardiovascular sensors.
Figure 13:
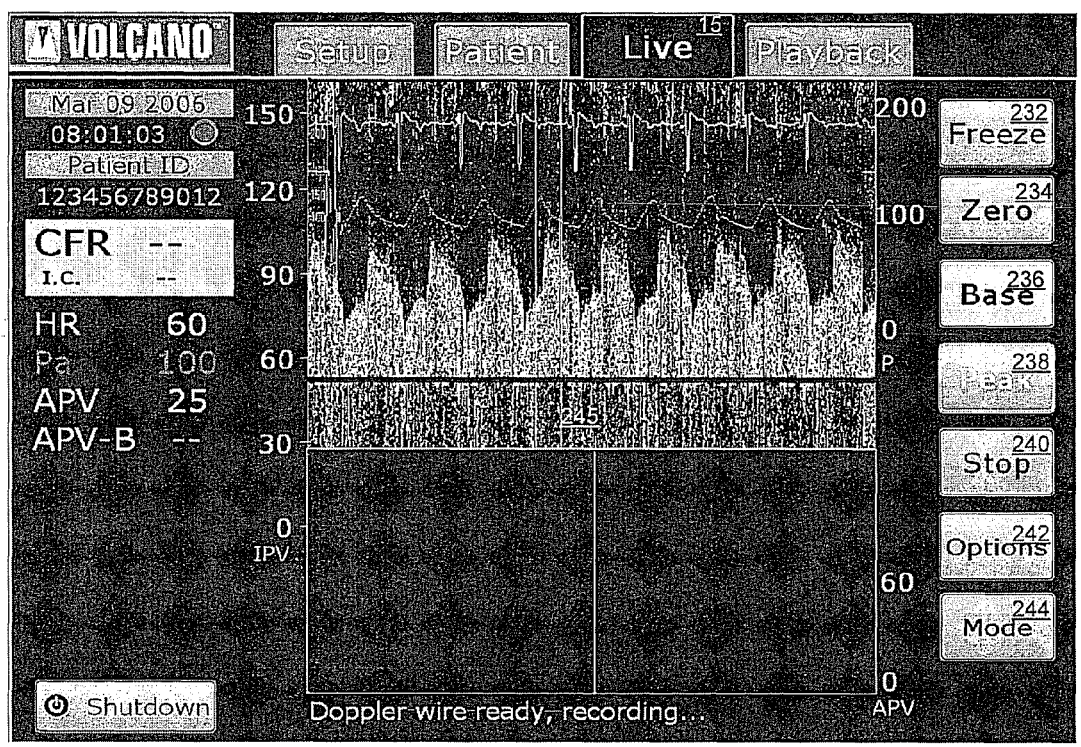
FIG. 13 illustrates an exemplary graphical user interface displaying flow data rendered by invasive cardiovascular sensors.

FIGS. 11 and 12 illustrate the Live 15 pressure display. The live pressure graph can display various pressures including Distal pressure, Aortic pressure, Distal pressure mean, Aortic pressure mean, Venous pressure and ECG. The Live sub-tab 15 is configured for Flow mode when only a Flow wire is connected to the system as illustrated in FIG. 13. The screen displays data variables on the left, graph and trend in the middle, and user buttons on the right. The exemplary interface includes Freeze 232—stop the chart scrolling, Zero 234—reset the aortic pressure input to 0 mmHg, Base 236—capture a snapshot of the baseline condition, Peak 238—capture a snapshot of the peak response condition, Rec/Stop 240—start/stop recording, Options 242—start the flow options dialog, Mode 244—switch between full screen, trend, and base and peak snapshot display.

In the illustrated embodiment Zero 234 is illuminated in green, indicating that the system recommends performing the zero operations, which resets the aortic pressure. This state is not shown in the figures. If the state were shown, while Zero 234 is green, Base 236 and Peak 238 would be faded, indicating that the user can not perform the base and peak operations until the zero operation has been performed. After zeroing the system, Base 236 (FIG. 13) is illuminated in green, indicating that base mode should be entered to capture a snapshot of the base condition. While Base 236 is green Peak 238 is faded, indicating that the peak operation should not be performed until after the base operation is completed. After the base 236 operation is performed, the Peak 238 option will be highlighted in green, indicating that the system recommends calculating or searching for the peak response.

A large number of live flow variables can be displayed on the Live pressure display for flow (FIG. 13). The interface can display the following variables: CFR—coronary flow reserve; IC/IV—hyperemic injection type; peak time—time of day of last peak detected; HR—heart rate; Pa—aortic pressure; APV—average peak velocity; APV-B—average peak velocity base; APV-P—APV last peak value; DSVR—diastolic/systolic velocity ratio; DSVR-B—base DSVR; DSVR-P—peak DSVR. In addition to displaying a large number of variables, the system can display a number of waveforms in the waveform portion 245 of the interface. Example waveforms include ECG, Aortic pressure, velocity spectra, IPV and trend. Additional variables and graphs are displayed in alternative embodiments.

FIG. 12 illustrates an exemplary live sub-tab in Combo mode. The Live Tab is configured for Combo mode when a Flow wire and a pressure wire are connected to the system. Also, the tab is configured for Combo mode when a Combo wire is connected to the system. The screen displays data variables on the left, graph and trend in the middle, and user buttons on the right. The Combo variables include: FFR—fractional flow reserve; CFR—coronary flow reserve; HSR—hyperemic stenosis resistance; HMR—hyperemic microvascular resistance; IC/IV—hyperemic injection type; peak time—time of day of last peak detected; HR—heart rate; Pa-Pd—gradient; Pd/Pa (NPR)—distal/aortic pressure ratio; Pa—aortic pressure mean; Pd—distal pressure mean; Pv—venous pressure mean; APV—average peak velocity; APV-b—average peak velocity—base; APV-p—average peak velocity—peak. Additionally, when the system is in Freeze 232 mode iPa, iPd and IPV can be displayed. In combo mode the graph 246 can display various types of data including IPV, Aortic pressure, Distal pressure, Mean aortic pressure, Mean distal pressure, velocity spectra, and ECG Entering the options 242 (FIG. 12) mode for the live pressure display allows the user to control the following options: Velocity Scale, Pressure Scale, Zero Offset, Scroll Speed, Search Mode (IC or IV), IPV Threshold, and Clear Trend.

Figure 14:
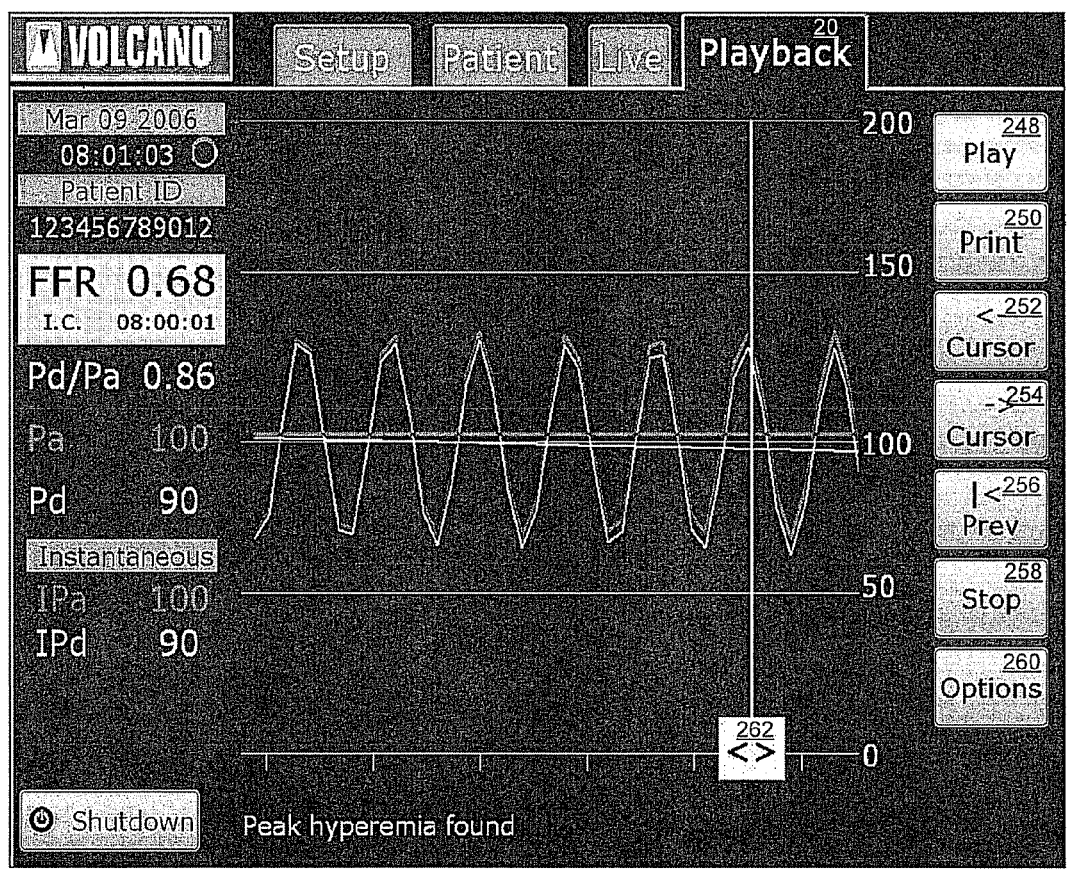
FIG. 14 illustrates an exemplary graphical user interface displaying recorded pressure data rendered by invasive cardiovascular sensors.
Figure 15:
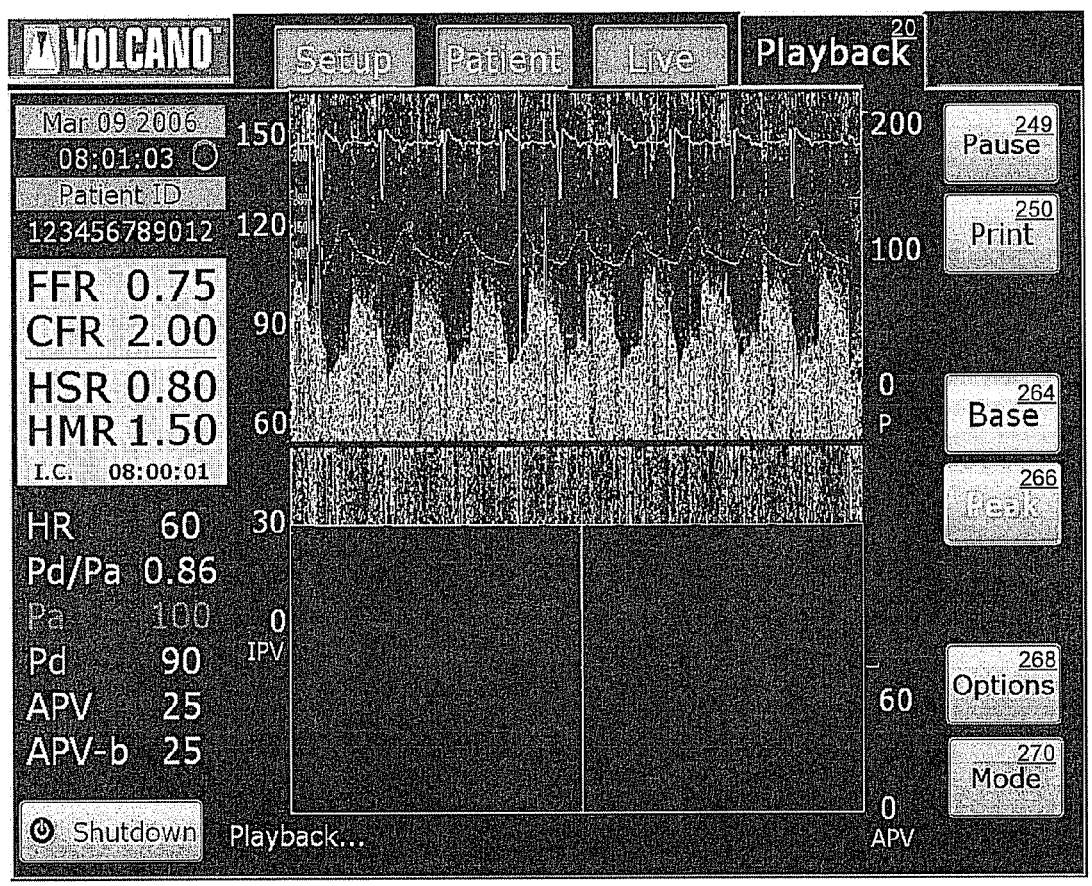
FIG. 15 illustrates an exemplary graphical user interface displaying recorded pressure and flow data rendered by invasive cardiovascular sensors.

FIG. 14 illustrates an exemplary Playback 20 sub-tab while frozen. The green Play 248 button indicates that the system recommends running the chart. The Playback Tab is configured for Pressure mode when playing back an archived file designated as a pressure study, or when playing back recorded data from the current study in which only a pressure wire is connected. The screen displays data variables on the left, graph in the middle, and user buttons on the right. The following options are available in Playback 20: Play—start playing the recording (or Pause to stop playing); Print—print a label or screen shot; Cursor<—move the cursor left; Cursor>—move the cursor right; Options—start Options Dialog;

While the Playback 20 sub-tab is displayed, a number of data pressure variables can be displayed. Example data pressure variables in Playback 20 mode include: FFR—fractional flow reserve; IC/IV—hyperemic injection type; HR—heart rate (only shown if ECG trace is selected); Pd/Pa—distal/aortic pressure ratio; Pa—aortic pressure; Pd—distal pressure. The Playback 20 pressure graph (FIG. 14) can display various types of data. For example Distal pressure, Aortic pressure, Distal pressure mean, Aortic pressure mean and an Investigation cursor 262 can all be displayed on the graph The Playback sub-tab 20 can also be configured to display flow data (FIG. 15). The Playback Tab is configured for Flow mode when playing back an archived file designated as a flow study, or when playing back recorded data from the current study in which only a flow wire is connected. The screen displays data variables on the left, graph and trend in the middle, and user buttons on the right. In flow mode the following variables can be displayed: HR—heart rate; CFR—coronary flow reserve/non-coronary flow reserve; APV—average peak velocity; DSVR—diastolic/systolic velocity ratio; Pa—aortic pressure. IPV, Aortic pressure, ECG, and velocity spectra can all be displayed as graphs.

The Playback sub-tab can also be configured to display combo data. The Playback Tab shall be configured for Combo mode when a Flow wire and a Pressure wire are connected to the system in the current study and playing back the current data, or when playing back an archived file designated as a Combo study. The screen shall display data variables on the left, graph and trend in the middle, and user buttons on the right. In Combo mode, a number of variables can be displayed, including FFR—fractional flow reserve; CFR—coronary flow reserve; HSR—hyperemic stenosis resistance; HMR—hyperemic microvascular resistance; IC/IV—hyperemic injection type; peak time—time of day last peak detected; HR—heart rate; Pd/Pa—distal/aortic pressure ratio; Pa—aortic pressure; Pd—distal pressure; APV—average peak velocity; APV-B—average peak velocity—base; APV-P—peak APV. The combo graph can display various flow and pressure data including IPV; Aortic pressure; Distal pressure; Mean aortic pressure; Mean distal pressure; velocity spectra and; ECG.

The system guides the user through various tasks. For example, referring to FIG. 12, a Zero 232 operation, Norm 235 operation, and Peak 238 operation can all be performed. When performing a Zero 232 operation, the button is initially green. After pressing the green Zero 232 button, the zeroing is accomplished, the Zero 232 becomes blue and the Norm 235 button turns green. When performing normalization, the Norm 235 button is initially green. After pressing the green Norm 235 button, normalization is accomplished, the button turns blue and the Peak 238 button turns green. To find the peak, the Peak 238 button is pressed after Norm 235. FFR is performed and the button Peak 238 turns green again, allowing the user to find another peak. While the Zero 232 button is green, the Norm 235 and Peak 238 buttons are faded, indicating that it is not appropriate to perform the norm or peak operations. Likewise, when the Norm 235 button is green, the Peak 238 button is faded, indicating that it is not appropriate to perform the peak operation. The faded system buttons prevent an operator from performing steps in the wrong order.

Figure 16:
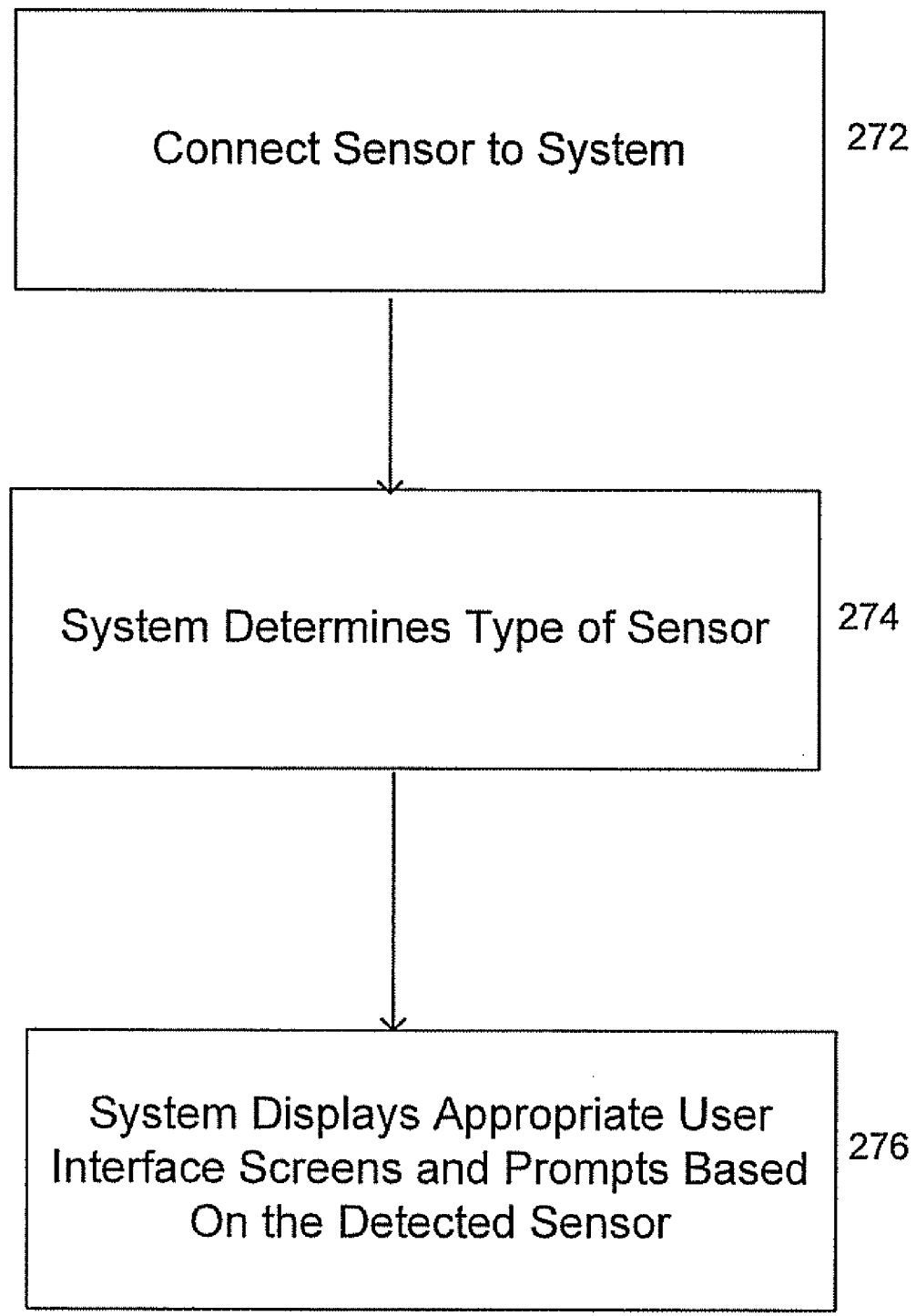
FIG. 16 is a flowchart summarizing a set of steps for displaying appropriate user interface screens based on the cardiovascular sensor connected to the system.

FIG. 16 is a flowchart summarizing an exemplary set of steps for displaying appropriate user interface screens based on the cardiovascular sensor connected to the system. Initially, a sensor connects to the system during step 272. Thereafter, during step 274, the system determines the type of sensor that was connected during step 272. In one embodiment, the system determines the type of sensor that was connected during step 272 by measuring a resistance value. In this embodiment each type of sensor has a unique resistance value and the system determines the type of sensor by matching the measured resistance value to the known resistance value of the sensor. In other embodiments, the system may read a value representing the type of sensor from a memory in the sensor. In still an alternative embodiment the sensor sends a packet of information identifying the sensor type to the system. In an exemplary embodiment the sensor is detected by measuring resistance values. If the measured resistance is not in the expected range then no sensor is connected to the system. In the exemplary embodiment, the system also reads an EPROM contained within the sensor that contains various calibration parameters. After determining the type of sensor connected, during step 276 the system displays appropriate user interface screens based on the sensor connected during step 272. For example, as noted above, the Live Tab 15 (FIG. 12) is configured for Combo mode when a Flow wire and a pressure wire are connected to the system.

Illustrative embodiments of the present invention and certain variations thereof have been provided in the Figures and accompanying written description. Those skilled in the art will readily appreciate from the above disclosure that many variations to the disclosed embodiment are possible in alternative embodiments of the invention. Such modifications include, by way of example, modifications to the form and/or content of the disclosed functions and functional blocks of the disclosed architecture, the measurements processed by the host system, the calculations arising from the measurements, the methods for setting modes and acquiring the measurements. Additionally, imaging data, such as Intravascular Ultrasound, Magnetic Resonance Imaging, Optical Coherence Tomography, etc., may be obtained, analyzed, and/or displayed upon the multipurpose application interface supported by the host system described hereinabove. The present invention is not intended to be limited to the disclosed embodiments. Rather the present invention is intended to cover the disclosed embodiments as well as others falling within the scope and spirit of the invention to the fullest extent permitted in view of this disclosure and the inventions defined by the claims appended herein below.

What is claimed is:

1. A multipurpose host system for invasive cardiovascular diagnostic measurement acquisition and display, the system comprising:

an external input signal bus interface for receiving data arising from one or more cardiovascular diagnostic measurement sensors attached to a flexible elongate member positioned within a vessel, the data being representative of at least one of pressure within the vessel and flow within the vessel;

a plurality of measurement processing components for receiving data from the one or more cardiovascular diagnostic measurement sensors attached to the flexible elongate member and rendering diagnostic measurement parameter values of at least one of the pressure within the vessel and the flow within the vessel according to the received data; and a multi-mode graphical user interface host comprising a set of diagnostic measurement user interfaces including display components corresponding to data output rendered by specified ones of the plurality of measurement processing components, the user interface simultaneously displaying a plurality of buttons associated with actions of the one or more cardiovascular diagnostic measurement sensors attached to the flexible elongate member;

wherein the user interface provides recommended action prompts automatically based on the data received from the one or more cardiovascular diagnostic measurement sensors attached to the flexible elongate member, the recommended action prompts providing visual indicators that guide a user through a series of actions by visually accentuating, in series, the plurality of buttons of the user interface associated with the actions of the one or more cardiovascular diagnostic measurement sensors attached to the flexible elongate member such that actuation of each of the plurality of buttons of the user interface results in the associated action of the one or more cardiovascular measurement sensors being executed;

wherein the multipurpose host system determines a sensor type for each of the one or more cardiovascular diagnostic measurement sensors connected to the multipurpose host system, wherein the simultaneously displayed plurality of buttons associated with the actions of the one or more cardiovascular diagnostic measurement sensors are based on the sensor type for each of the one or more cardiovascular diagnostic measurement sensors.

2. The multipurpose host system of claim 1 wherein the user interface visually accentuates a particular button of the plurality of simultaneously displayed buttons associated with a particular action of the series of actions by displaying at least one other button of the plurality of simultaneously displayed buttons in a way indicating that execution of the action associated with the at least one other button is prevented.

3. The multipurpose host system of claim 2, wherein the user interface visually accentuates the particular button of the plurality of simultaneously displayed buttons associated with the particular action of the series of actions by displaying the particular button in a way indicating that execution of the particular action associated with the particular button should be performed.

4. The multipurpose host system of claim 1 wherein the user interface displays data rendered by the sensors attached to the external input signal bus interface.

5. The multipurpose host system of claim 1 wherein the user interface does not display diagnostic measurement user interfaces unless the relevant sensors are attached to the external input signal bus interface.

6. The multipurpose host system of claim 1 wherein the cardiovascular diagnostic measurement sensors include a blood pressure processing sensor and a blood velocity sensor.

7. The multipurpose host system of claim 6 wherein the blood pressure processing sensor and the blood velocity sensor are integrated into a single combination sensor.

8. The multipurpose host system of claim 7 wherein the user interface displays user interfaces relevant to both the blood pressure processing sensor and the blood velocity sensor.

9. The multipurpose host system of claim 1 further including a record module that may be activated to record data rendered by the sensors attached to the external input signal bus interface.

10. The multipurpose host system of claim 9 further including a playback module for viewing data recorded by the record module.

11. The multipurpose host system of claim 1, wherein the multipurpose host system determines the sensor type for each of the one or more cardiovascular diagnostic measurement sensors by measuring a resistance value on a line connecting the cardiovascular diagnostic measurement sensor to the multipurpose host system.

12. The multipurpose host system of claim 1, wherein the multipurpose host system determines the sensor type for each of the one or more cardiovascular diagnostic measurement sensors by obtaining information from the cardiovascular diagnostic measurement sensor regarding its sensor type and wherein the user interface adjusts its display to include data related to the determined sensor type.

13. The multipurpose host system of claim 12, wherein the information obtained from the cardiovascular diagnostic measurement sensor further includes calibration parameters for the cardiovascular diagnostic measurement sensor.

14. An adaptive graphical user interface for a multipurpose host system for invasive cardiovascular diagnostic measurement acquisition and display, the interface comprising:
   a settings module for viewing and editing sensor calibration data for a plurality of sensors attached to a flexible elongate member and configured for positioning within a vessel of a patient to monitor a pressure within the vessel and a flow within the vessel;
   a viewing module for viewing, in real time, data rendered by the plurality of sensors while the flexible elongate member is positioned within the vessel of the patient, the viewing module automatically displaying a plurality of action buttons pertinent to the plurality of sensors attached to the flexible elongate member simultaneously and automatically indicating recommended actions to a user of the multipurpose host system based on data received from the plurality of sensors, wherein the recommended actions comprise a plurality of actions to be performed in series to obtain data from the plurality of sensors representative of the pressure within the vessel and the flow within the vessel, and wherein the recommended actions are automatically indicated to the user in series by selectively visually accentuating one or more of the simultaneously displayed plurality of action buttons of the user interface associated with performing each of the recommended actions, and wherein the viewing module determines the plurality of action buttons pertinent to the sensors based on the types of sensors attached to the flexible elongate member.

15. The interface of claim 14 further including a playback module to view recorded data rendered by at least one of the plurality of sensors.

16. The interface of claim 14 wherein the viewing module does not display action buttons pertinent to a sensor type unless the relevant sensor type is attached to the multipurpose host system.

17. The interface of claim 14 wherein the plurality of sensors are cardiovascular diagnostic measurement sensors.

18. The interface of claim 17 wherein the cardiovascular diagnostic measurement sensors include a blood pressure processing sensor and a blood velocity sensor.

19. The interface of claim 18 wherein the blood pressure processing sensor and the blood velocity sensor are integrated into a single combination sensor.

20. The interface of claim 14 wherein the multipurpose host system determines the types of sensors attached to the host system by measuring the resistance value on a line connecting each of the plurality of sensors to the host system.

21. The interface of claim 14 wherein the multipurpose host system reads calibration parameters thr each of the plurality of sensors attached to the host system from a memory connected to the host system with the sensor.

* * * * *